United States Patent
Hein

(10) Patent No.: US 7,149,276 B2
(45) Date of Patent: Dec. 12, 2006

(54) SYSTEM, METHOD, AND COMPUTER PROGRAM PRODUCT THAT CORRECTS MEASURED DATA

(75) Inventor: Ilmar A. Hein, Schaumburg, IL (US)

(73) Assignees: Kabushiki Kaisha Toshiba, Tokyo (JP); Toshiba Medical Systems Corporation, Otawara (JP)

( * ) Notice: Subject to any disclaimer, the term of this patent is extended or adjusted under 35 U.S.C. 154(b) by 329 days.

(21) Appl. No.: 10/890,238

(22) Filed: Jul. 14, 2004

(65) Prior Publication Data

US 2006/0013353 A1    Jan. 19, 2006

(51) Int. Cl.
*G21K 1/12* (2006.01)
(52) U.S. Cl. .......................................... 378/4
(58) Field of Classification Search .................. 378/40, 378/4, 16, 145, 901, 101, 113; 382/250, 382/600
See application file for complete search history.

(56) References Cited

U.S. PATENT DOCUMENTS

| | | | |
|---|---|---|---|
| 5,165,100 A | 11/1992 | Hsieh et al. .................. 382/6 |
| 5,825,842 A * | 10/1998 | Taguchi ....................... 378/15 |
| 2004/0130470 A1 * | 7/2004 | Gregoire ..................... 341/139 |
| 2006/0109950 A1 * | 5/2006 | Arenson et al. ............... 378/4 |

* cited by examiner

*Primary Examiner*—Edward J. Glick
*Assistant Examiner*—Alexander Taningco
(74) *Attorney, Agent, or Firm*—Oblon, Spivak, McClelland, Maier & Neustadt, P.C.

(57) ABSTRACT

An x-ray computed tomography system, method, and computer product that generates an x-ray beam with an x-ray generator and detects with an x-ray detector at least one characteristic of the x-ray beam generated by the x-ray generator, after the x-ray beam has passed through an object, the system including a converting unit configured to obtain analog projection data outputted by the x-ray detector and to convert the analog projection data to digital projection data, and a processing unit configured to obtain the digital projection data from the converting unit, to detect overflow digital projection data that overflows a measuring range of the computed tomography system, and to correct the overflow digital projection data of the digital projection data by using a curve fitting function.

48 Claims, 13 Drawing Sheets

SYSTEM, METHOD, AND COMPUTER PROGRAM PRODUCT THAT CORRECTS MEASURED DATA

BACKGROUND OF THE INVENTION

1. Field of the Invention

The present invention relates generally to correcting measured data that is affected by errors and deviates from real data.

2. Discussion of the Background

An x-ray computed tomography (CT) imaging device is shown in FIG. 1, and the CT device includes a gantry 1 that accommodates a rotating ring 2, an x-ray source 3 that generates an x-ray cone-beam, and an x-ray filter 4. The gantry 1 has an array type x-ray detector 5 including a variety of detector elements 5A arranged in 1-D or 2-D rows. Other arrangements of the detector elements 5A of the x-ray detector 5 are also possible. FIG. 2 shows 10 rows each having 1,000 detector elements with an x-ray flux shown schematically emitted from a focal point F.

The x-ray source 3 and the array detector 5 are installed on a rotating ring 2 and face opposite sides of a subject (not shown), which lays on a sliding bed 6. Each detector element 5A of the array detector 5 corresponds to a channel. The x-ray source 3 is directed to the subject through the x-ray filter 4 and a high voltage generator 7 activates the x-ray source 3 when an x-ray controller 8 supplies a trigger signal. The high voltage generator 7 applies a high voltage to the x-ray source 3 with a timing with which the trigger signal is received. This causes the x-rays to be emitted from the x-ray source 3 and a gantry/batch controller 9 synchronously controls a revolution of the rotating ring 2 of the gantry 1 and the sliding of the sliding bed 6. A system controller 10 constitutes the control center of the entire system and controls the x-ray controller 8, the gantry/batch controller 9, the bed 6, and rotates the rotating ring 2 around a desired path around the subject while the subject is irradiated by the x-ray source 3.

The detector elements 5A of the array detector 5 are capable of measuring an intensity of the x-ray generated by the x-ray source 3, with and without the subject being interposed between the x-ray source 3 and the detector elements 5A. The detector elements 5A are also capable of measuring other characteristics of the x-ray from which an image of the subject is constructed. Thus, each detector element (channel) 5A measures at least an x-ray intensity and outputs an analog output signal corresponding to that intensity. The output signals from the channels are inputted to a data collection unit 11, which amplifies the signals for each channel and converts the signals to digital signals to produce digital projection data. The digital projection data is output from the data correction unit 11 and is fed to a processing unit 12. Based on the digital projection data corresponding to each channel, the processing unit 12 preprocesses and reconstructs an image corresponding to the subject placed on the sliding bed 6.

Conventional electronic data acquisition systems employ analog detectors or transducers coupled to analog-to-digital (A/D) converters to record physical signals in a digital format. The detectors and/or the A/Ds have a limited input parameter signal range over which they can accurately record a physical parameter of interest, for example the intensity of the x-ray beam. When the input parameter signal level is higher than a maximum signal range (maximum input level ($S_{DMax}$)) of the detector or A/D, the detector or A/D output signal (measured data) can no longer accurately reproduces the input signal (real data), and the detector or A/D output "clips." When the detector or A/D output clips, a problem appears in the background art because the signal output of the detector or A/D remains constant over time, as long as the input parameter signal has a level higher than the maximum input level.

Thus, irrespective of a change in the input parameter signal (that corresponds to a change of the physical parameter of interest), if the changed input parameter signal is still higher than the maximum input level, the signal output of the detector or A/D is constant. In other words, the detector or A/D is unable to detect the "real" value of the physical parameter of interest and instead detects the maximum input level $S_{DMax}$. The maximum input level $S_{DMax}$ is a characteristic of device, and thus various devices will degrade the real data in different ways. The condition of the detector or A/D being unable to detect the real value of the physical parameter of interest is referred throughout this disclosure as an "overflow" condition, and this condition is applicable to other electrical units than the detector or the A/D.

The output from the detector or A/D may be processed by a number of steps in a processing chain to produce reconstruction data and a profile of the reconstruction data changes at different steps along the processing chain although the signal output of the detector or A/D is constant. The final result of the processing will be inaccurate and incorrect when the overflow condition exists. Thus, a problem appears for any device that measures an input parameter and based on that measurement creates or recreates an image of an object because the final recreated image of the object will be different under overflow conditions than the real object.

In a specific example of an x-ray CT, overflow conditions exist at least in one of the detectors or the A/Ds and these conditions cause artifacts to appear in the reconstructed images of various objects. Thus, there is a problem that the artifacts diminish the quality of the end product of the CT, blurring parts of the object examined by the CT and/or creating dark ring images. Accordingly, the results of the background art x-ray CT systems could not produce reconstructed images without ghosts and false characteristics, rendering the x-ray CT images less reliable for diagnosing various patient conditions.

SUMMARY OF THE INVENTION

One object of the present invention is to provide a system, a method, and a computer program product for correcting input data that overflows a measuring range of the system by using a curve fitting algorithm.

Another object is to provide a system, a method, and a computer program product that detects overflow data and corrects the overflow data by using a combination of curve fitting algorithms.

A further object of the present invention is to provide a system, a method, and a computer program product that detects overflow data and corrects the overflow data by selecting a combination of curve fitting algorithms and prior knowledge data.

Thus, according to one aspect of the present invention, there is provided an x-ray computed tomography system that generates an x-ray beam with an x-ray generator and detects with an x-ray detector at least one characteristic of the x-ray beam generated by the x-ray generator, after the x-ray beam has passed through an object, including a converting unit configured to obtain analog projection data outputted by the x-ray detector and to convert the analog projection data to digital projection data, and a processing unit configured to obtain the digital projection data from the converting unit, to detect overflow digital projection data that overflows a measuring range of the computed tomography system, and to correct the overflow digital projection data of the digital projection data by using a curve fitting function.

According to another aspect of the present invention, there is provided a novel method for correcting an image of an object placed in an x-ray computed tomography system that generates an x-ray beam with an x-ray generator and detects with an x-ray detector at least one characteristic of the x-ray beam generated by the x-ray generator, after the x-ray beam has passed through the object, including converting analog projection data outputted by the x-ray detector to digital projection data with a converting unit connected to the x-ray detector, detecting overflow digital projection data that overflows a measuring range of the computed tomography system with an overflow detecting unit connected to the converting unit, and correcting the overflow digital projection data with a correction unit connected to the overflow detecting unit by using a curve fitting function to produce the corrected image.

According to another aspect of the present invention, there is provided a novel computer program product for correcting an image of an object placed in an x-ray computed tomography system that generates an x-ray beam with an x-ray generator and detects with an x-ray detector at least one characteristic of the x-ray beam generated by the x-ray generator, after the x-ray beam has passed through the object, the computer program product storing instructions for execution on a computer system, which when executed by the computer cause the computer to execute a process including converting analog projection data outputted by the x-ray detector to digital projection data with a converting unit connected to the x-ray detector, detecting overflow digital projection data that overflows a measuring range of the computed tomography system with an overflow detecting unit connected to the converting unit, and correcting the overflow digital projection data with a correction unit connected to the overflow detecting unit by using a curve fitting function to produce the corrected image.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, which like reference numerals refer to identical or corresponding parts throughout the several views, and in which.

DETAILED DESCRIPTION OF THE PREFERRED EMBODIMENTS

Figure 1:
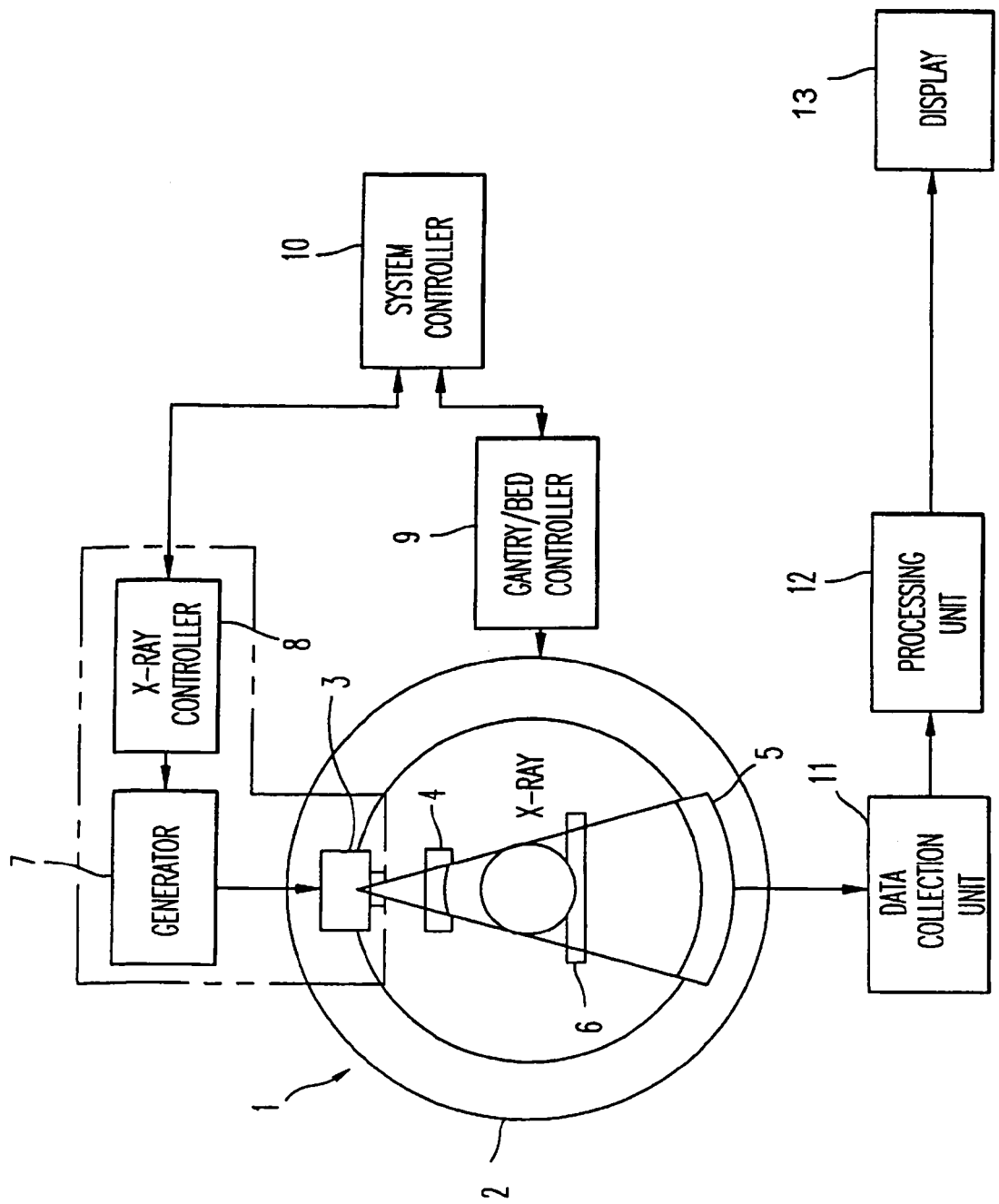
FIG. 1 is a diagram of an x-ray CT device.
Figure 3:
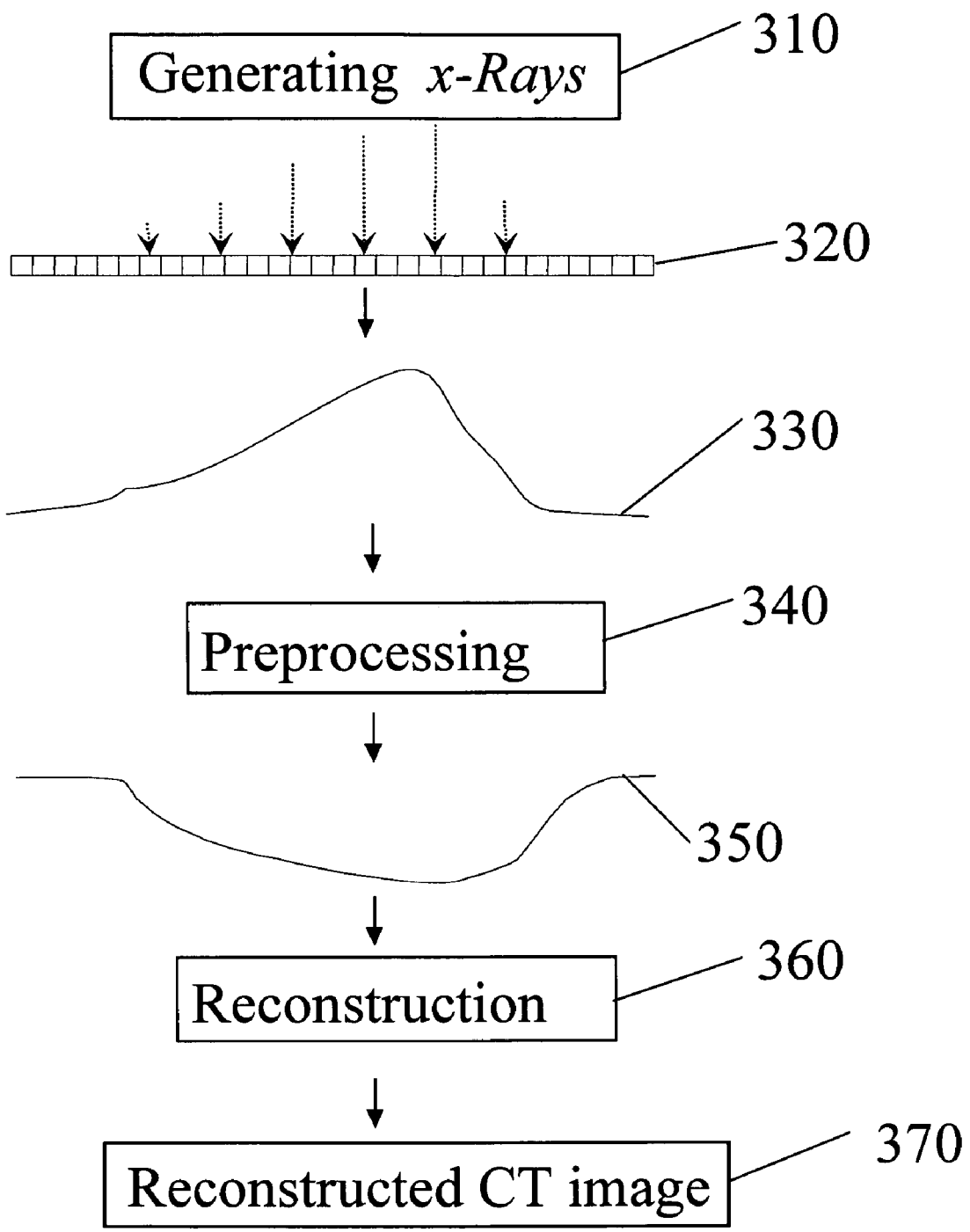
FIG. 3 is a diagram showing a reconstruction process based on measured data.

The preferred embodiments of the present invention will be described below with reference to the drawings. FIG. 3 shows the steps of a method for irradiating an object with x-ray radiation and reconstructing an image of the object based on detected x-ray radiation, when the object is placed in the x-ray CT described in FIG. 1.

Figure 2:
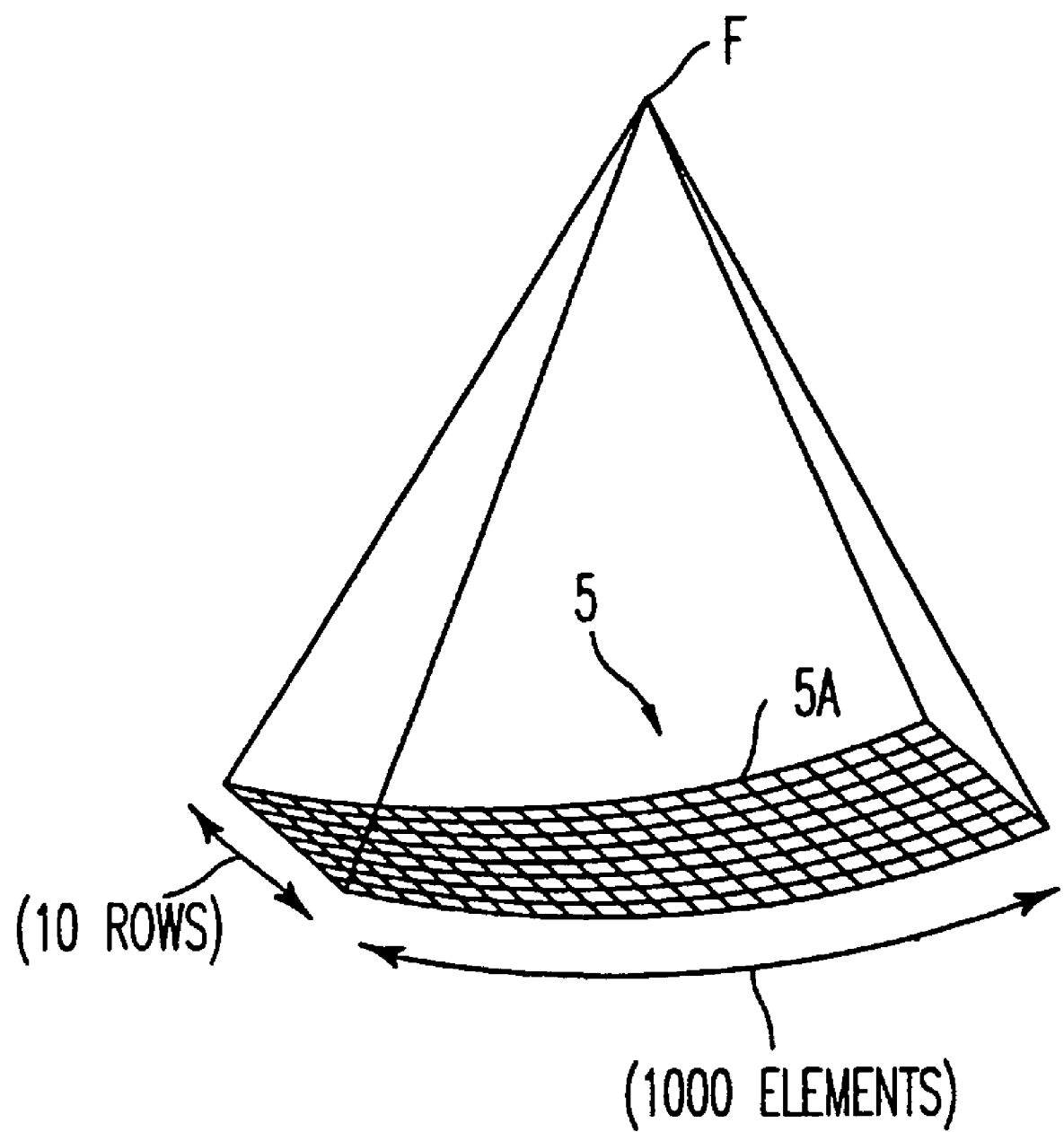
FIG. 2 is a perspective view of a two-dimensional array x-type detector of FIG. 1.

In step 310, x-ray radiation is generated by the x-ray source 3 of the x-ray CT and irradiated towards the array detector or plurality of detectors 5 shown in FIG. 2. The detector or the A/D generates in step 320 a signal corresponding for example to the intensity of the x-ray radiation received by the detector. Various combinations of detectors have been discussed regarding FIG. 2.

In step 330, the output of the detector elements 5A, after being collected by the data collection unit 11, are digitized to form an x-ray profile of the detector or A/D data, in preparation of the next steps of the process to be applied. This digitized data is called "pure" data because it reflects pure measured data without any processing, and includes errors produced by the detector.

In step 340, various processes generically called preprocessing are applied to the digitized data obtained in step 330. The preprocessing includes but is not limited to reference and offset correction, water calibration sensitivity disparity correction, etc. The preprocessing is applied to the digitized x-ray profile for removing some of the errors present. However, the preprocessing of step 340 does not remove the errors attributed to the overflow condition discussed above. Other preprocesses are disclosed in U.S. Pat. No. 5,825,842, which content is included in its entirety hereby by reference.

The result of the preprocessing step 340 is used in step 350 for producing reconstruction data. The reconstruction data has a different profile than the digitized data. In step 360 the reconstruction of the irradiated object is determined based on the reconstruction data obtained in step 350. The reconstruction step 360 assembles together the data from all the channels of the detector 5 and step 370 produces the final, reconstructed, CT image of the object.

In another embodiment, the data collection unit 11 and the processing unit 12 collect data from many rows of detectors, and the processing unit 12, based on all the data collected by the data collection unit 11, produces the final, reconstructed, CT image and displays that image on the display 13. However, due to the overflow condition discussed above, the reconstructed CT image has spurious features, which hide the real features of the subject.

Figure 4:
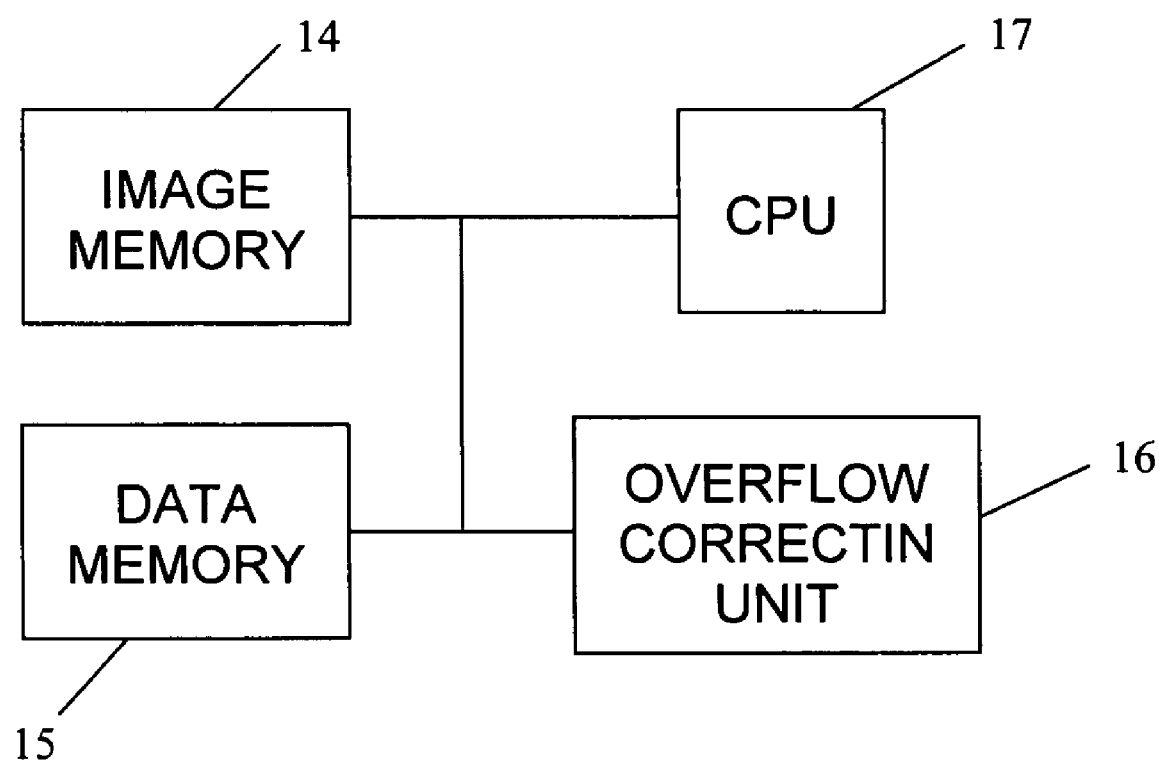
FIG. 4 is a diagram of a reconstruction processor and units included therein according to the invention.

A diagram of the reconstruction processor 12 is shown in more detail in FIG. 4. Projection data from the collection unit 11 is stored in data memory 15, and image memory 14 is provided for storing the reconstructed image data or for storing the image data that is being reconstructed. Memories 14 and 15 can be implemented as a RAM or other semiconductor memory known by one skilled in the art of computer memories. An overflow correction unit 16 includes at least a polynomial unit, a spline unit, and a prior knowledge unit, and also may include a weighting unit. The functions of these units will be discussed with reference to FIG. 5. Units 14–16 and their operations are controlled by CPU 17. CPU 17 can determine the overflow points and carry out desired processing on the projection data obtained from the data collection unit 11, to correct the overflow condition.

Figure 5:
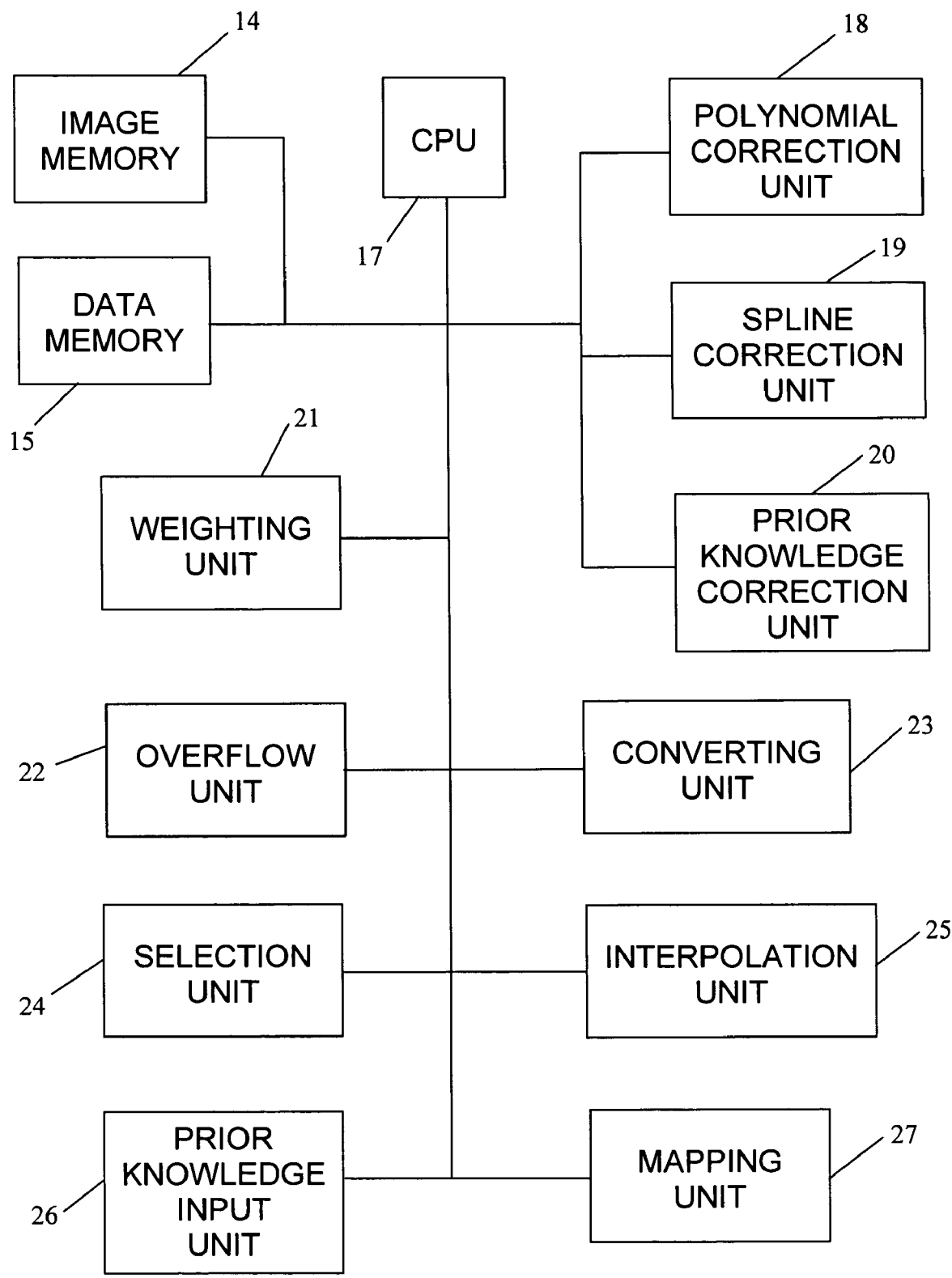
FIG. 5 is a diagram showing in more detail the reconstruction processor and units of FIG. 4.

A more detailed diagram of another construction of the reconstruction processor 12 is shown in FIG. 5. The image memory 14 and the data memory 15 are connected to the CPU 17. Also connected to, and controlled by CPU 17, are a polynomial unit 18, a spline unit 19, a prior knowledge unit 20, a weighting unit 21, an overflow unit 22, a converting unit 23, a selection unit 24, an interpolation unit 25, a prior knowledge input unit 26, and a mapping unit 27. The polynomial and spline units 18 and 19, respectively, perform overflow corrections and the weighting unit 21 performs an overflow correction using a combination of an output from the polynomial unit 18 and an output from the spline unit 19. The processor 12 shown in FIGS. 4 and 5 could be implemented in hardware as a dedicated microcomputer, or could be implemented in software. For example the overflow correction unit 16 could be implemented as a semiconductor gate array.

Figures 6A, 6B:
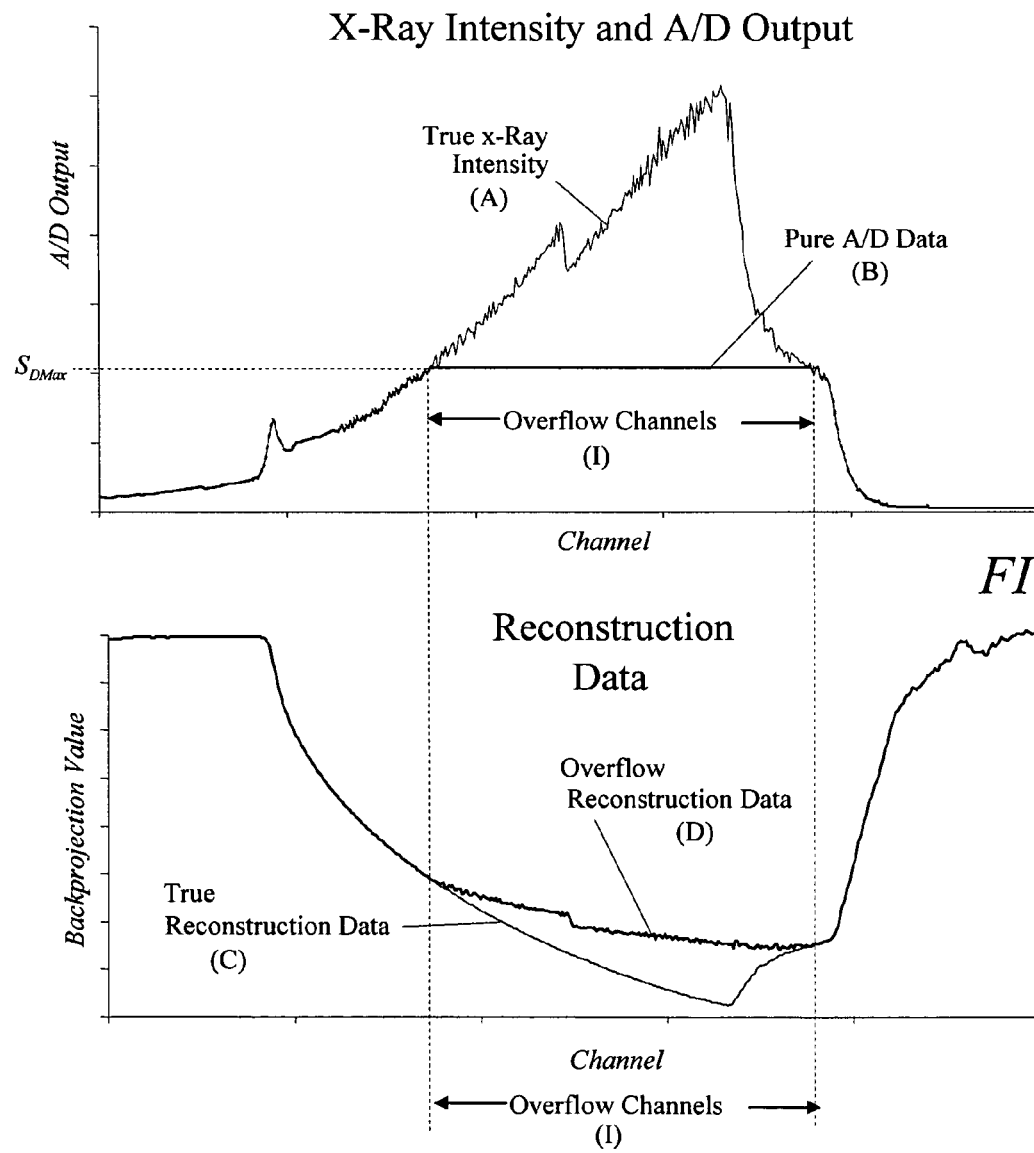
FIGS. 6A and 6B are schematic views of measured and reconstruction data, respectively, having overflow points.

In a particular example that is not intended to limit the embodiments of the present invention, FIGS. 6(A) and 6(B) show plots of measured x-ray intensity detected by the x-ray detector and reconstruction data reconstructed by the processor 12, respectively. More specifically, FIG. 6(A) shows the x-ray intensity measured by detectors and digitized by A/Ds plotted versus the channels that measure the x-ray intensity. Curve (A) shows the true x-ray intensity (the real values of the x-ray intensity) produced by the x-ray source 3, and curve (B) shows the "pure" A/D data or the measured and digitized data. As can be seen in FIG. 6(A), region (I) of the true x-ray intensity is different than the same region of the measured x-ray intensity because of the overflow condition. When the overflow is present, the real values of the x-ray intensity are replaced in the measured data with a value equal to the maximum input level $S_{DMax}$, producing a flat profile.

FIG. 6(B) shows the reconstruction data produced in step 360 discussed above. Curve (C) corresponds to the true reconstruction data (based on true x-ray intensity values (A)), and shows a profile that is different than a profile of the overflow reconstruction data that corresponds to curve (D), which is reconstructed based on the measured data (B). FIG. 6(A) shows that the measured data (B) has a flat portion where the detector or A/D is not capable of measuring the real value of the x-ray intensity and that flat portion could be identified in a collection of data by the "flat" characteristic. However, the overflow reconstruction data (D) does not have the "flat" characteristic, which makes it difficult to identify overflow channels when analyzing the overflow reconstruction data (D).

The overflow reconstruction data (D) has two characteristics that are discussed next. First, the overflow reconstruction data (D), which includes overflow points, is not clipped or constant in region (I), as the measured x-ray intensity (B), but has a profile that exhibits noise and may have discontinuities. This profile causes ring artifacts in the reconstructed images produced by the processing unit 12 and displayed on the display 13.

Second, the magnitude of the overflow reconstruction data (D) is higher than the magnitude of the true reconstruction data (C) (data without overflow points). The effect of this characteristic in the reconstructed images is a darkening and potential loss of physiological structure in the final CT image.

Figure 7:
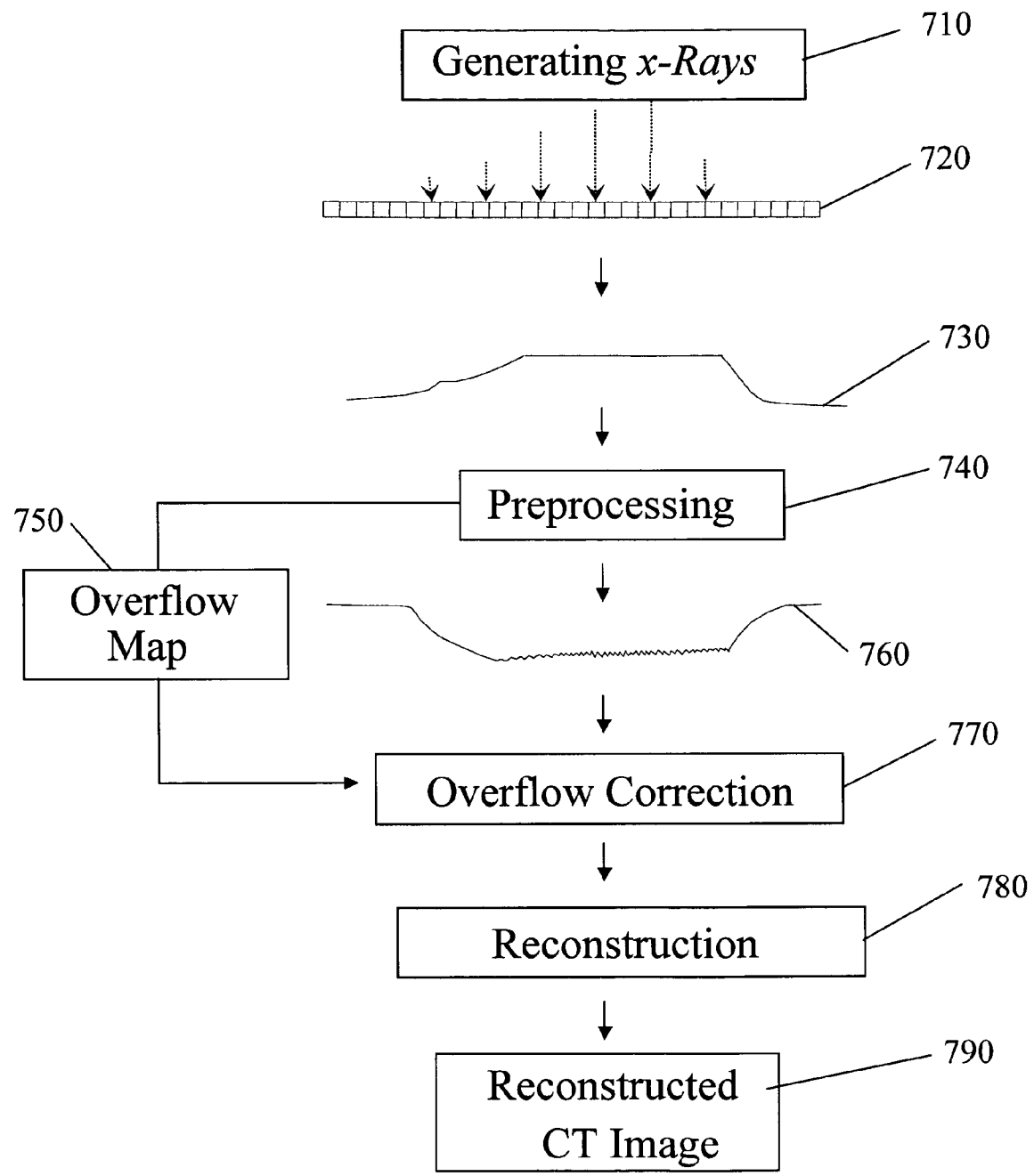
FIG. 7 is a diagram showing a reconstruction process having implemented an overflow correction process.

FIG. 7 illustrates a process of reconstruction of a CT image that identifies overflow points and corrects those points based on various algorithms. This process has some of the steps similar to the steps of FIG. 3, and therefore those steps are not described here. In the current embodiment, the process shown in FIG. 7 is implemented on a row-by-row basis in terms of the detector elements (in other embodiments it can be implemented on a column basis, or on a temporal basis with a single detector). Further, in the current embodiment, the overflow correction step 770 takes place after the preprocessing step 740. The overflow correction step 770 is placed in this order because in some applications it is not feasible to implement the overflow correction before preprocessing due to hardware speed constraints or other constraints. In other embodiments, where speed is not a factor, the overflow correction step can be placed before the preprocessing step.

As discussed above, when a level of the x-ray intensity measured by a detector is beyond the maximum signal range for which the detector is capable of detecting the x-ray intensity, the detector clips and a false value is output by the detector, as long as the overflow condition is maintained. To correct the false values introduced by the clipped detectors, the process of FIG. 7 identifies the overflow points (see for example those points in curve (B), region (I), of FIG. 6(A)) and creates a map of the overflow points. Because it is not possible to determine the overflowing points, when the overflow condition is present, directly from the reconstruction data obtained in step 760, the preprocessing step 740 creates the overflow map in step 750, based on the pure A/D data (B) shown in FIG. 6(A). The overflow map is a binary map indicating which channels of the x-ray detector are in the overflow condition. The overflow map is used in the next steps, when applying the overflow correction to the overflow points.

In step 770, the overflow correction is applied to those values of the reconstruction data that correspond to channels that are in the overflow condition, as specified by the overflow map created in step 750. After the overflow correction step 770 corrects the reconstruction data of step 760, the reconstruction step 780 constructs the image of the object and displays in step 790 the reconstructed CT image of the object on the display 13.

Figure 8:
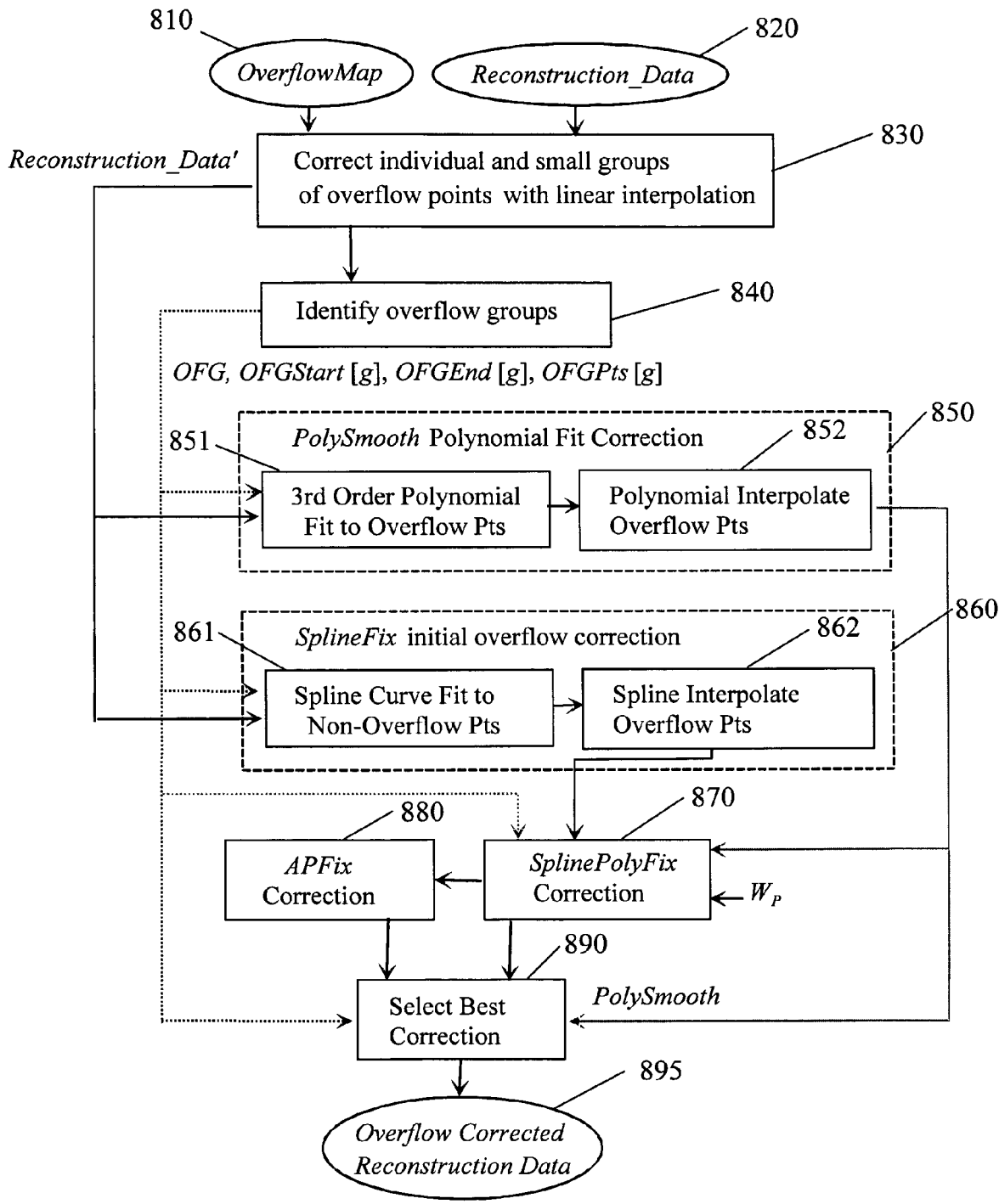
FIG. 8 is a diagram showing in more detail the overflow correction process of FIG. 7.

In this way, the method, system, and computer program product of the present invention correct the ring artifacts, the darkening, and the potential loss of physiological structure in the reconstructed image that plague the background art systems. The inventors of the present invention have found that the overflow correction step 770 could be implemented by a variety of mathematical algorithms. One possible way is described in the embodiment shown in FIG. 8. FIG. 8 shows a block diagram corresponding to the overflow correction step 770 of FIG. 7. Based on the overflow map 810, and the reconstruction data 820 obtained in step 760 of FIG. 7, individual and small groups of overflow points are identified and corrected in step 830, for example based on a linear interpolation.

Step 830 produces a new reconstruction data set Reconstruction_Data' by correcting only the individual and small groups of overflow points. The larger groups of overflow points are not corrected in step 830.

Figure 9:
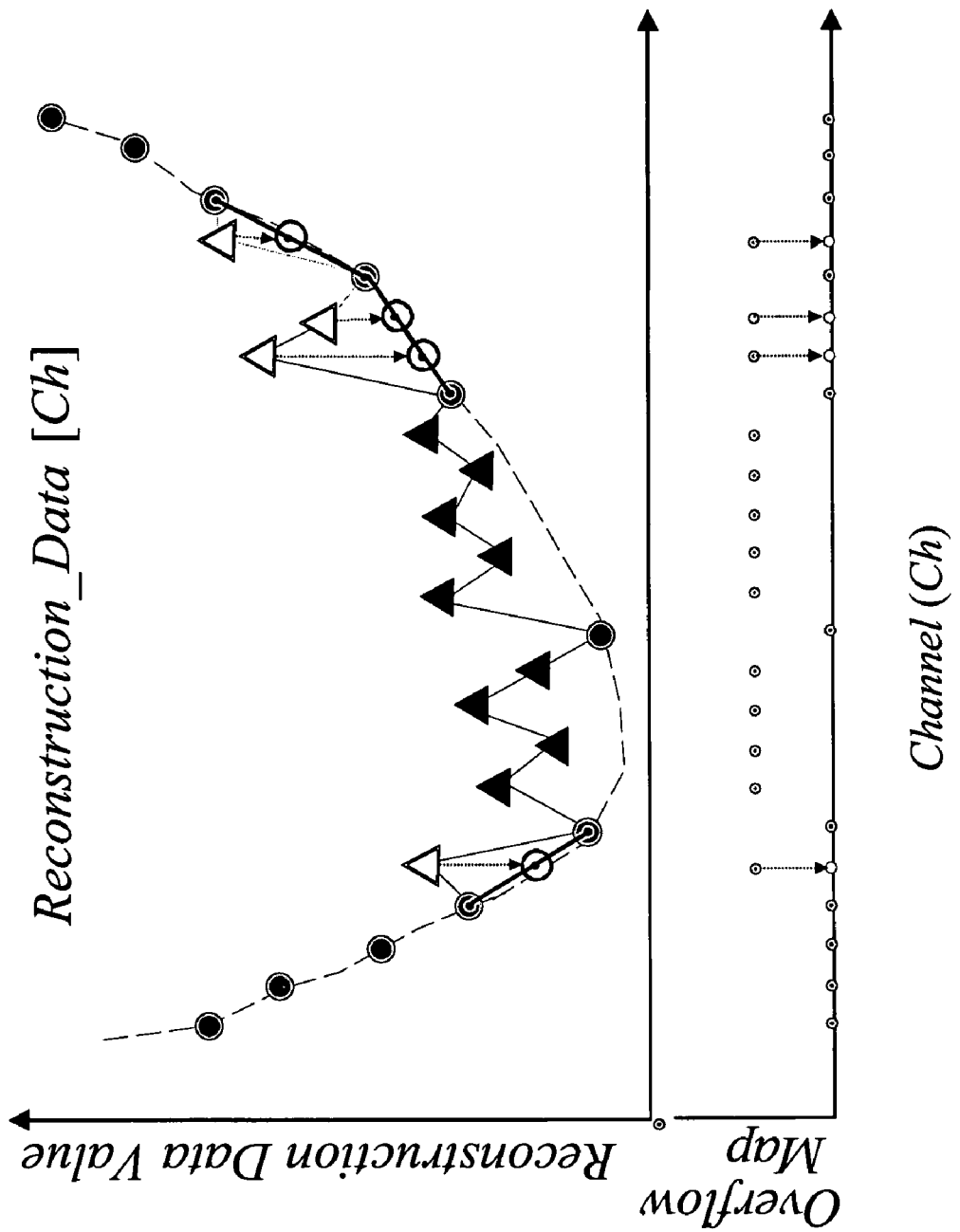
FIG. 9 is a schematic view of a correction process of individual and small groups of overflow points of measured data.

For a better understanding of step 830, FIG. 9 shows a diagramatical view of the overflow map 810 and the reconstruction data 820. The overflow map, positioned in the lower part of FIG. 9, shows each channel of the array detector 5 along the x-axis. An empty circle denotes an overflow point that was corrected by interpolation in step 830, the lower solid circles correspond to original non-overflow points, and the upper solid circles correspond to overflow points yet to be corrected.

The values of the reconstruction data Reconstruction_Data' are shown in the upper part of FIG. 9. An empty triangle indicates an overflow point that has been corrected by linear interpolation based on the values of the non-overflow points bordering the overflow point, and a solid triangle indicates overflow points that will be corrected by another procedure than a linear interpolation. The dashed line indicates a non-overflow curve, which is unknown for overflow conditions. One target of the process described in FIG. 8 is to bring the overflow points as close as possible to the non-overflow curve.

According to step 830, the linear interpolation correction is applied to those overflow points that respect a condition that a number of consecutive overflow points is less than a predetermined minimum consecutive overflow points Min_Consecutive_Overflow_Pts number. The Min_Consecutive_Overflow_Pts number is determined depending on the accuracy desired. The smaller the number, the better the accuracy of the process. The Min_Consecutive_Overflow_Pts number is two in the example shown in FIG. 9. FIG. 9 shows three regions in which the overflow points are corrected using the linear interpolation. After the linear interpolation is performed in step 830, the overflow map is updated to reflect the corrected overflow points and the updated map is input in step 840 to identify groups of overflow points that do not respect the condition for the Min_Consecutive_Overflow_Pts number. Also, the reconstruction data provided at step 820 is updated with the corrected overflow points and is provided to other steps.

Figure 10:
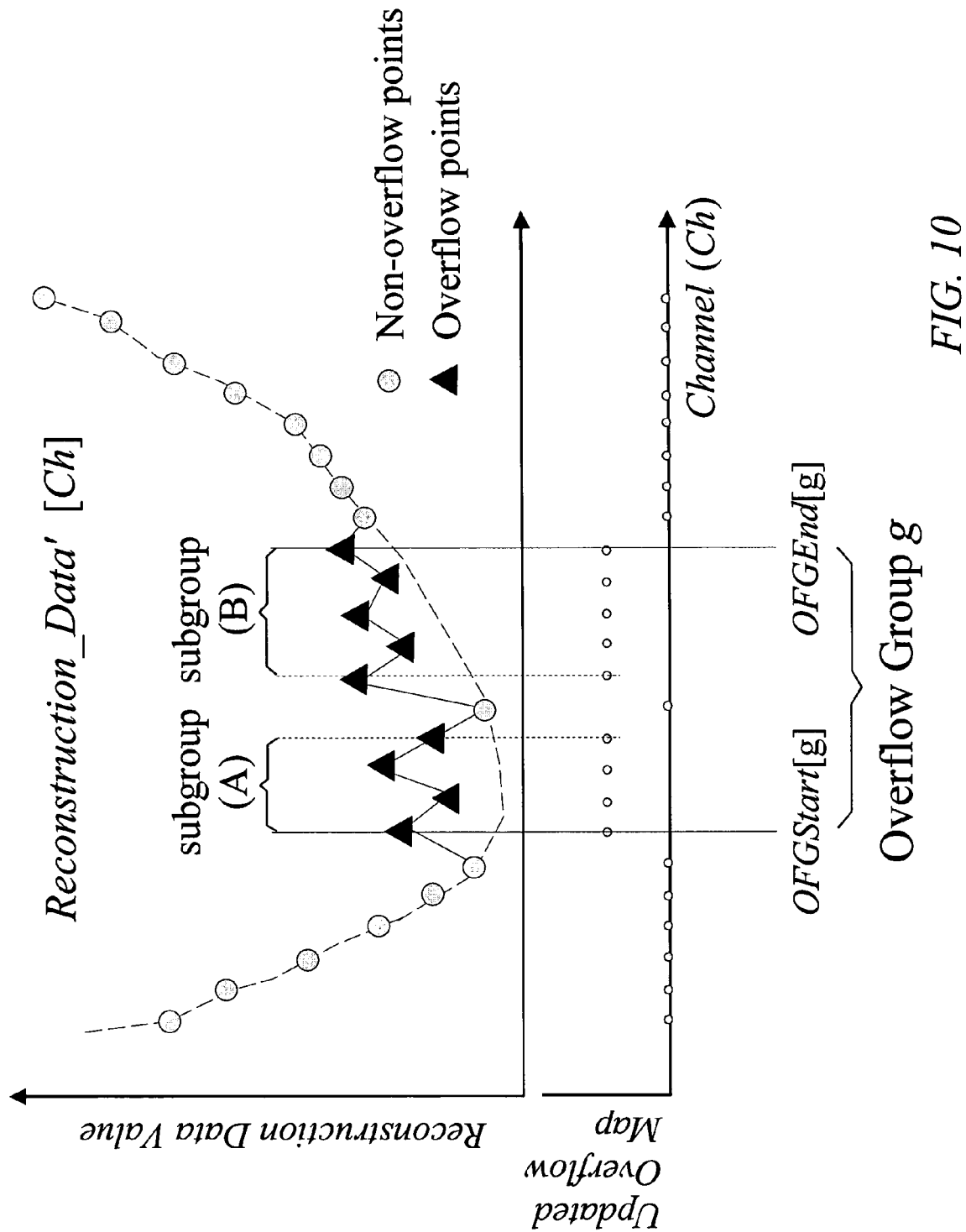
FIG. 10 is a schematic view showing groups and subgroups of overflow points in a collection of measured points.

In step 840, the process identifies groups of overflow points in the updated reconstruction data Reconstruction_Data', based on a procedure that will be discussed next. FIG. 10 shows multiple groups of overflow points that are present in a row of channels. Considering a row of channels at a time, a total number of overflow groups in a respective row of channels is denoted OFG. An overflow group "g" of the multiple groups of overflow points is shown for example in FIG. 10. The position of the overflow group "g" is defined by a start point OFGStart[g] and by an end point of the group denoted OFGEnd[g]. The number of overflow points in the group "g" is OFGPts[g], and is given by the expression:

$$OFGPts[g]=OFGEnd[g]-OFGStart[g]+1 \qquad (1)$$

A series of consecutive overflow points is considered a subgroup of a group if a number of non-overflow points MinGroupSpacing separating the consecutive overflow points is smaller or equal to a predetermined value. For example, in FIG. 10, MinGroupSpacing is set to one and two subgroups (A) and (B) are part of the same group "g" because the number of non-overflow points between the two subgroups is one, which is less than MinGroupSpacing. Thus, for a predetermined MinGroupSpacing, if a plurality of subgroups have between adjacent subgroups a number of non-overflow points less or equal to the MinGroupSpacing, the plurality of subgroups are considered one single group.

However, in another embodiment of the present invention, the subgroups shown in FIG. 10 could correspond to different groups. By selecting the groups and subgroups in a certain way, a better curve-fit could be achieved. Further, FIG. 10 shows that a non-overflow point could be part of an overflow group (here one non-overflow point is part of the overflow group "g").

Figure 11:
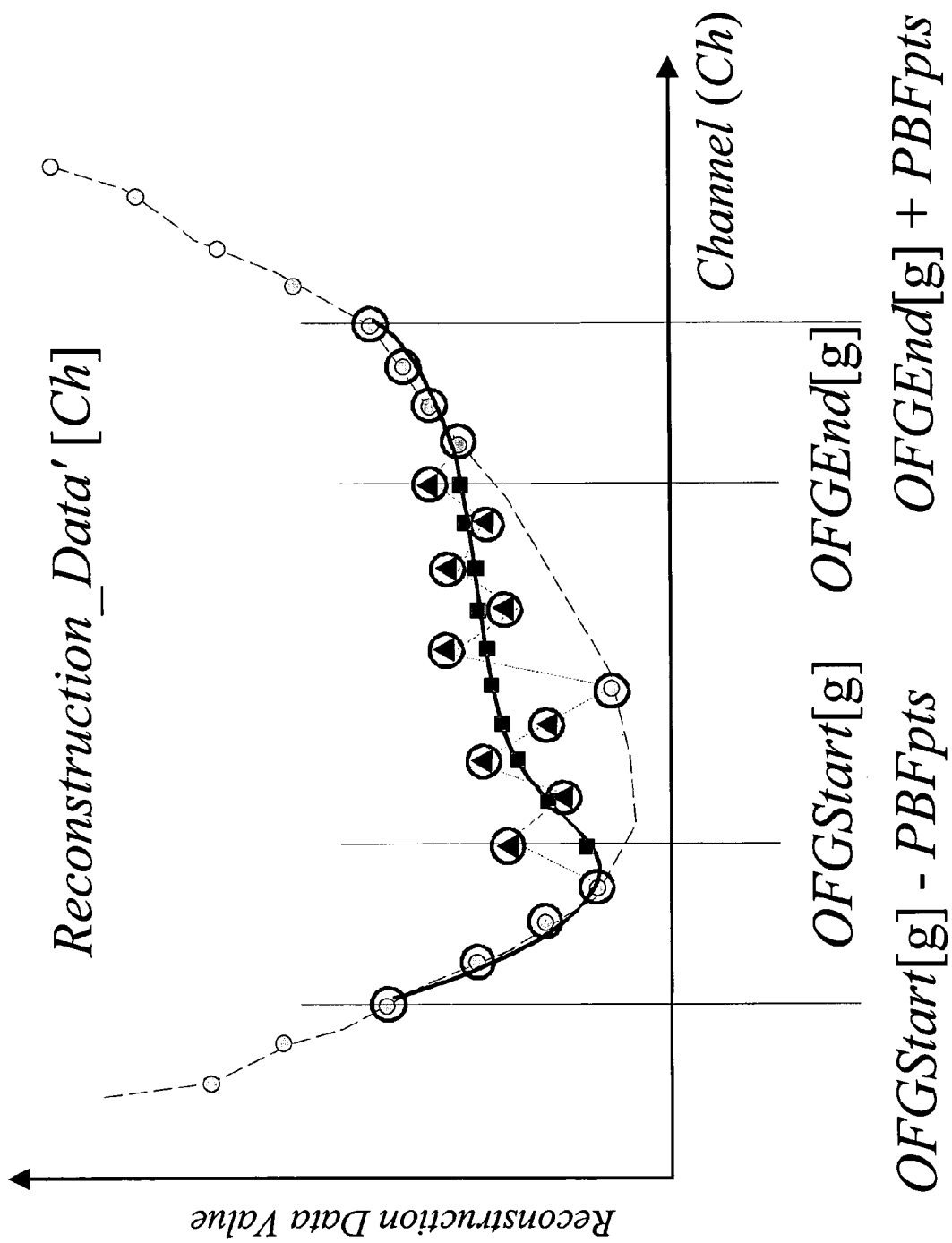
FIG. 11 is a schematic view of smoothing data by applying a polynomial curve fit to overflow and non-overflow points.

After the OFG, OFGStart[g], OFGEnd[g], and OFGPts[g] are determined in step 840, various corrections are applied to the identified overflow groups. In step 850, a polynomial correction is applied to the overflow groups identified and defined in step 840. In the present embodiment, the overflow data is smoothened by fitting a polynomial of order $N_p$ as shown in FIG. 11. However, in another embodiment of the present invention a different type of curve or low-pass filter is used to smooth the overflow data.

FIG. 11 shows that polynomials are fitted to the group "g" found in the Reconstruction_Data'[n] for those points (channels) that obey the expression:

$$OFGStart[g]-PFBpts \leq n \leq OFGEnd[g]+PFBpts \qquad (2)$$

where PFBpts is the number of non-overflow points bounding the overflow group "g" on each side of the group "g."

The PFBpts number is selected depending on various factors that will be discussed later. The polynomial correction is of the form:

$$PolyFit_g[ch] = \sum_{a=0}^{N_p-1} C_g[a] \cdot Ch^a \qquad (3)$$

where $C_g[a]$ is the ath polynomial coefficient for the fit of group "g." A general least-squares fit of the data in the overflow group to the polynomial equation (3) is used to obtain the polynomial coefficients $C_g[a]$, i.e, $$C_g[a]=\text{Least squares fit of } \{(OFGStart[g], \text{Reconstruction\_Value}[OFGStart[g]]), \ldots, (OFGEnd[g], \text{Reconstruction\_Value}[OFGEnd[g]])\} \qquad (4)$$

to a polynomial of order $N_p$.

A correction PolySmooth using the polynomial defined by equation (3), is given by:

$$PolySmooth[Ch] = PolyFit_g[Ch] \qquad (5)$$

If $OFGStart[g] \leq Ch \leq OFGEnd[g]$ $PolySmooth[Ch] = \text{Reconstruction\_Data}[Ch]$ Otherwise The PolySmooth correction does not interpolate or estimate the correct values of the overflow points in the Reconstruction_Data', but only smoothens out overflow regions, which removes ring-type artifacts in the reconstructed images. FIG. 11 shows a solid line indicating the result of the PolySmooth correction based on (i) the non-overflow points bordering the overflow group "g," and (ii) the overflow points of the overflow group "g." The solid line is not identical to the dash line that indicates the true reconstruction data discussed in FIG. 9.

Step 850 could include a plurality of substeps and FIG. 8 shows for example two substeps 851 and 852. Substep 851 determines a third order polynomial fit for the overflow points in the overflow group "g" and step 852 interpolates the overflow points and substitutes them with a polynomial curve produced in substep 851 to better approximate the values of the real data.

The process described in FIG. 8 is not limited to applying a polynomial fit 850 after the overflow groups have been identified in step 840. For example, FIG. 8 shows that the overflow correction process can go from step 840 to either step 860 in which a spline fit is applied to the overflow groups or to step 870 in which a combination of correction methods are applied.

Step 860 is similar to step 850 with a difference that another mathematical correction is applied. Step 860 could include a plurality of steps or two steps as shown in FIG. 8. In the example shown in FIG. 8, which is not intended to limit the present embodiment of the invention to only two steps, a step 861 determines a spline curve that is fitted to non-overflow points and an output of step 861 is inputted to a step 862 in which a spline interpolation is applied to the non-overflow points bordering the overflow groups.

In one embodiment of the present invention, the spline curve is fit to non-overflow points bordering each side of the group "g" of the Reconstruction_Data'. The spline curve is given by:

$$SplineCurve_g[Ch] = SplineFit(\text{Reconstruction\_Data}[m]) \quad (6)$$

where $$OFGStart[g] - SFpts \le m < OFGStart[g] \text{ and} \quad (7)$$
$$OFGEnd[g] < m \le OFGEnd[g] + SFpts$$

The spline fit is applied in this example to a total of 2·SFpts points that are found in the intervals defined by equation (7), the spline fit is applied until all the overflow points are corrected, and SFpts represents a number of non-overflow points bordering the overflow group "g." In the current system, it was not possible for an overflow group to be located at the edge of the detector. In the general case, groups located at the edge of the detector will be extrapolated.

Figure 12:
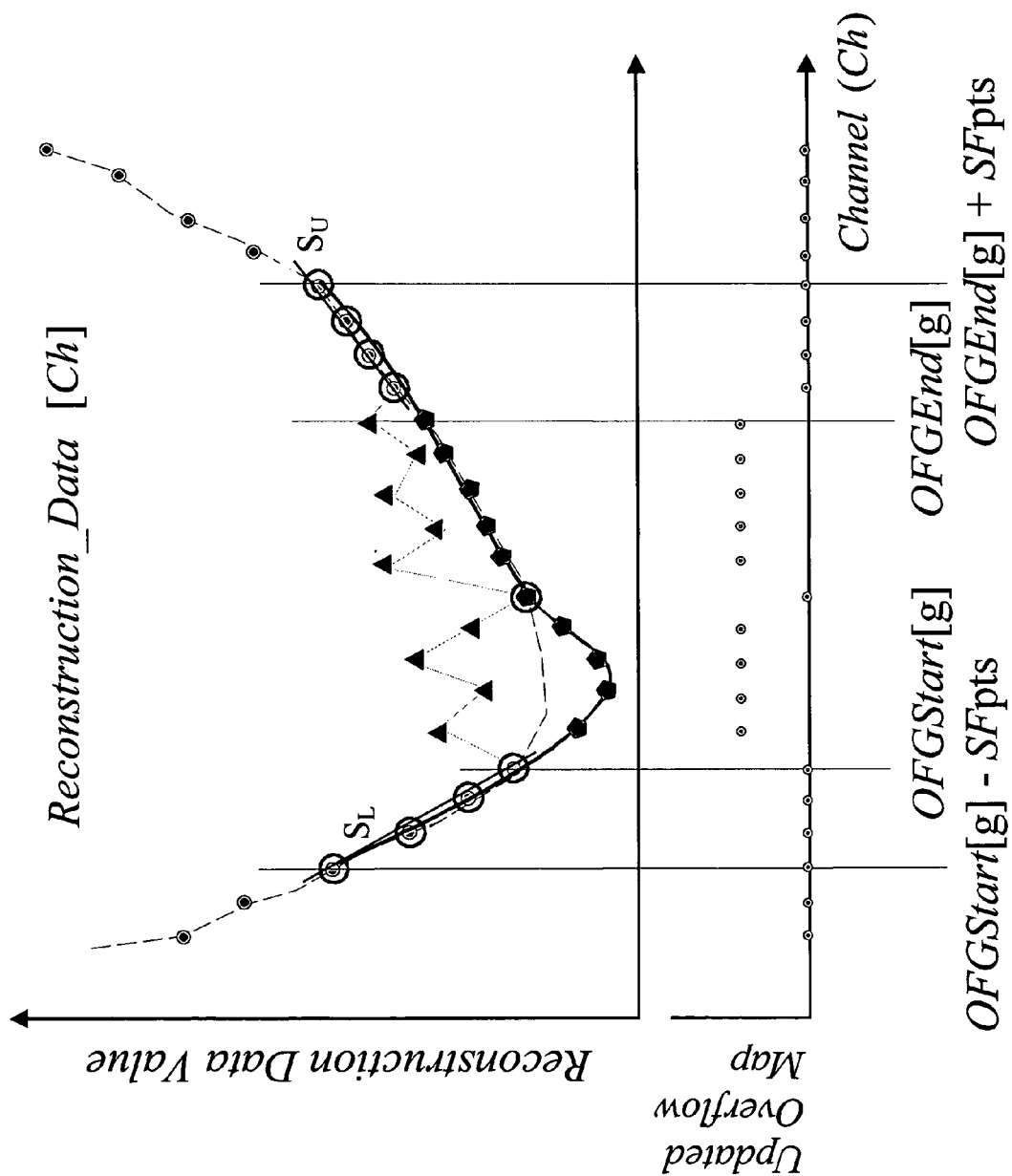
FIG. 12 is a schematic view of a spline fit and interpolation applied to non-overflow points.

The SplineCurve$_g$[Ch] curve corresponding to channels "Ch" is shown in FIG. 12 as a solid line, which is different than the dash line that corresponds to the real value of the reconstruction data. The updated overflow map is used for correcting all the overflow points in the overflow group "g." In FIG. 12, the empty circle indicates the non-overflow points used to spline fit the SplineCurve$_g$[Ch] curve, and the solid pentagons represent the corrected overflow points using the SplineCurve$_g$[Ch] curve. After the spline fit has been applied to the overflow points of the group "g," the overflow map is updated and the process is repeated for the remaining overflow groups until all the overflow groups are corrected.

The SplineFix correction is given by:

$$SplineFix[Ch] = SplineCurve_g[Ch] \quad (8)$$

If $OFGStart[g] \le Ch \le OFGEnd[g]$ $$SplineFix[Ch] = \text{Reconstruction\_Data}[Ch]$$

Otherwise

The process shown in FIG. 8 is not limited only to PolySmooth or SplineFix corrections, but other mathematical correction algorithms could be used to correct the overflow points of the overflow groups. In general, the true reconstruction data is unknown when the overflow condition is present, and thus it is very difficult to generate a perfect correction. The SplineFix generates a general correction of the overflow data, and sometimes, the magnitude of the SplineFix correction will overcorrect or undercorrect the A/D data, which will introduce new artifacts into the final reconstructed images.

The inventors of the present invention have found that a combination of PolySmooth and SplineFix produces an improved correction. In one embodiment of the present invention, an adaptive weighted average of the two corrections (PolySmooth and SplineFix) is implemented in step 870 in FIG. 8. Step 870 receives an output from the PolySmooth correction step 850 and an output from the SplineFix correction step 860. Based on these two outputs, a new correction SplinePolyFix is calculated as will be described further. However, in other embodiments of the present invention, a non-adaptive weighted or other functions, such as a weighted multiplication of the two, may be used to combine the two corrections or any other corrections.

Regarding the present embodiment, a magnitude of the spline curve correction is a function of slopes $S_L$ and $S_U$ of the non-overflow data, where $S_L$ is the slope of the non-overflow points on the lower side of the group (smaller channel values; left side of the overflow group in figures) and $S_U$ is the slope on the upper side of the group (larger channel values; right side of overflow group in figures). The PolySmooth and SplineFix corrections are combined using an adaptive weight $W_P$ determined by the maximum slope of the two slopes $S_L$ and $S_U$. In another embodiment, $W_P$ is a function of a variety of overflow parameters, such as both slopes $S_L$ and $S_U$, the number of points OFGPts in the overflow group "g," or combinations of parameters.

In this embodiment, the combination of the PolySmooth and SplineFix is SplinePoly and is given by:

$$SplinePoly[p] = \frac{W_P(S_M) \cdot PolySmooth[p] + SplineFix[p]}{W_P(S_M) + 1} \quad (9)$$

where $S_M$ is the maximum slope of the slopes $S_L$ and $S_U$:

$$S_M = \text{Max}(S_L, S_U). \quad (10)$$

In the current embodiment, $S_L$ and $S_U$ are calculated by:

$$S_L = \frac{\text{Reconstruction\_Data}[P_{L2}] - \text{Reconstruction\_Data}[P_{L1}]}{P_{L2} - P_{L1}} \quad (11)$$

and $$S_U = \frac{\text{Reconstruction\_Data}[P_{R2}] - \text{Reconstruction\_Data}[P_{R1}]}{P_{R2} - P_{R1}} \quad (12)$$

where $$P_{L1} = OFGStart[g] - SFBpts \quad (13)$$

$$P_{L2} = OFGStart[g] - 1 \quad (14)$$

$$P_{R1} = OFGEndt[g] + 1 \quad (15)$$

and $$P_{R2}=OFGEnd[g]+SFBpts. \tag{16}$$

As can be seen in equations (11)–(16), the slopes $S_L$ and $S_U$ are calculated for non-overflow points bordering an overflow group.

In the current embodiment, $W_p(S_M)$ is determined by simulation as follows. Non-overflow data (pure data) is either generated by simulation or acquired experimentally, and then this pure data is processed to produce non-overflow Reconstruction_Data. The non-overflow pure data is then modified by simulation to produce overflow data, to account for the overflow condition. This overflow data is processed to produce overflow Reconstruction_Data. Because both the non-overflow and overflow Reconstruction_Data are known, "true" values of $W_p$ as a function of $S_m$ are calculated. For example, different $S_m$ are calculated from a set of modified non-overflow pure data and corresponding $W_p$ values are determined by simulation by fitting overflow reconstruction data to the non-overflow reconstruction data. In the current embodiment, the two sets of $S_m$ and $W_p$ calculated by simulation are plotted together on a graph and a least-squares linear curve is fit for the $W_p$ versus $S_m$ data to produce the adaptive weighting function according to equation:

$$W_p(S_M)=m \cdot S_M+b, \tag{17}$$

where m and b are the slope and intercept, respectively, determined by the least-squares fit. In other embodiments, a different fitting function or a lookup table can be used for determining $W_p(S_M)$.

The SplinePolyFix correction produces a correction having the characteristics of a spline curve scaled to statistically match the non-overflow data. This correction will produce an improved reconstructed image with fewer and reduced overflow artifacts.

Further improvements of the process described in FIG. 8 could be achieved by using prior knowledge data regarding how the preprocessing step 740 in FIG. 7 influences the non-overflow data. In the general case, prior knowledge data can be calibration data, a mathematical function, or a combination of both. In the case of the x-ray CT, for example, the preprocessing step could include water calibration, which introduces a distinct curved shape frequently having a vertex in the reconstruction data, as shown for example in FIG. 6(B) in the true reconstruction data (C). The position of the bottom vertex and the slope of the curve on both sides of the vertex is a function of the water calibration data used in the preprocessing step and of the position of the overflow group in the row of channels. The water calibration data is constant and is known prior to determining any correction.

The SplinePolyFix correction determined in step 870 can be combined with a prior knowledge data (such as some general knowledge about the attenuation of object being scanned, such as head or abdomen) obtained in step 880 to produce a better correction APFix:

$$APFix=F\{SplinePoly, prior knowledge\}, \tag{18}$$

where APFix is the overflow correction with the prior knowledge, and F{ } is a function that combines the Spline-Poly and the prior knowledge data; such as a weight that scales SplinePoly based on the prior knowledge.

The SplinePolyFix and APFix corrections estimate true data values of the overflow points. Under certain conditions (such as noise), it is possible for the APFix and/or Spline-PolyFix to produce corrected values that are worse than the overflow data for a particular overflow group. This produces new undesirable artifacts in corrected images.

Thus, in step 890, a selection of the best correction among the corrections already discussed is determined. The Spline-PolyFix and APFix corrections are compared with the PolySmooth correction to determine whether the corrections are valid. The validity of the corrections are determined if any SplinePolyFix or APFix corrected point within an overflow group is greater than the corresponding PolySmooth corrected point. If the above discussed condition is valid, then the correction is considered invalid. The flags for APFixValid and SplinePoly Valid are set according to the following algorithm:

APFixValid=1
SplinePolyValid=1
for (i=OFGStart[g]; i<OFEnd[g]; i++) {
  if (APFix[i]>PolySmooth[i]) APFixValid=0;
  if (SplinePoly]>PolySmooth[i])SplinePolyValid=0;}, where "1" indicates valid and "0" indicates invalid.

The best correction for the overflow group "g" is determined according to Table 1:

TABLE 1

Output correction selection

| Correction Validity Flag | | Overflow corrected reconstruction data |
|---|---|---|
| APFixValid[g] | SplinePolyValid[g] | for group g |
| 0 | 0 | PolySmooth |
| 0 | 1 | SplinePoly |
| 1 | 0 | APFix |
| 1 | 1 | APFix |

However, other embodiments can use different criteria for determining the validity of a correction and a selection of the best correction is then implemented.

Finally, in step 895 all the overflow points of the reconstruction data are corrected based on the results of Table 1 and the input from the selection step 890, and the reconstructed image of the object is displayed on the display.

Any embodiment of the present invention conveniently may be implemented using a conventional general purpose computer or microdisc processor program according to the teachings of the present invention, as would be apparent to those skilled in the computer art. Appropriate software may already be prepared by programmers of ordinary skill based on the teachings of the present disclosure, as would be apparent to those skilled in the software art.

Figure 13:
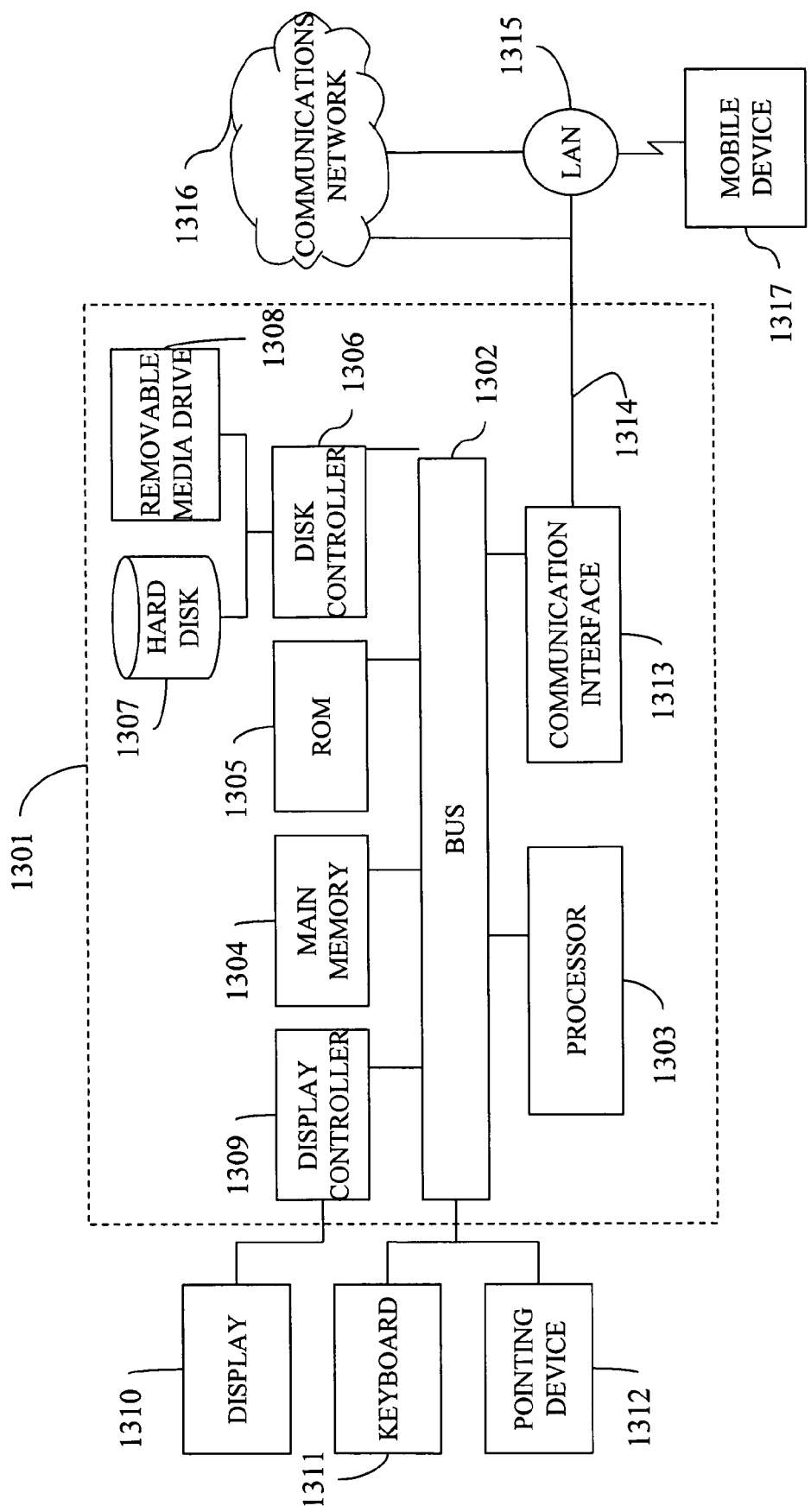
FIG. 13 is a schematic view of a general purpose computer.

FIG. 13 is a schematic illustration of a general purpose computer 1300 which can be programmed according to the teachings of the present invention. In FIG. 13, the computer 1300 can be used to implement the processes of the present invention, wherein the computer includes, for example, a display device 1302 (e.g., a touch screen monitor with a touch-screen interface, etc.), a keyboard 1304, a pointing device 1306, a mouse pad or digitizing pad 1308, a hard disk 1310, or other fixed, high density media drives, connected using an appropriate device bus (e.g., a SCSI bus, an Enhanced IDE bus, an Ultra DMA bus, a PCI bus, etc.), a floppy drive 1312, a tape or CD ROM drive 1314 with tape or CD media 1316, or other removable media devices, such as magneto-optical media, etc., and a mother board 1318. The mother board 1318 includes, for example, a processor 1320, a RAM 1322, and a ROM 1324 (e.g., DRAM, ROM, EPROM, EEPROM, SRAM, SDRAM, and Flash RAM, etc.), I/O ports 1326 which may be used to couple to an image acquisition device and optional special purpose logic devices (e.g., ASICs, etc.) or configurable logic devices (e.g., GAL and re-programmable FPGA) 1328 for performing specialized hardware/software functions, such as sound processing, image processing, signal processing, neural network processing, automated classification, etc., a microphone 1330, and a speaker or speakers 1332.

As stated above, the system of the present invention includes at least one computer readable medium. Examples of computer readable media are compact discs, hard disks, floppy disks, tape, magneto-optical disks, PROMs (EPROM, EEPROM, Flash EPROM), DRAM, SRAM, SDRAM, etc. Stored on any one or on a combination of computer readable media, the present invention includes software for controlling both the hardware of the computer and for enabling the computer to interact with a human user. Such software may include, but is not limited to, device drivers, operating systems and user applications, such as development tools. Such computer readable media further includes the computer program product of the present invention for performing any of the processes according to the present invention, described above. The computer code devices of the present invention can be any interpreted or executable code mechanism, including but not limited to scripts, interpreters, dynamic link libraries, Java classes, and complete executable programs, etc.

The programming of general purpose computer 1300 may include a software module for digitizing and storing images obtained from film or an image acquisition device. Alternatively, the present invention can also be implemented to process digital data derived from images obtained by other means, such as a picture archive communication system (PACS). In other words, the digital images being processed may be in existence in digital form and need not be converted to digital form in practicing the invention.

Accordingly, the mechanisms and processes set forth in the present description may be implemented using a conventional general purpose microprocessor or computer programmed according to the teachings in the present specification, as will be appreciated by those skilled in the relevant art(s). Appropriate software coding can readily be prepared by skilled programmers based on the teachings of the present disclosure, as will also be apparent to those skilled in the relevant art(s). However, as will be readily apparent to those skilled in the art, the present invention also may be implemented by the preparation of application-specific integrated units or by interconnecting an appropriate network of conventional component units.

The present invention thus also includes a computer-based product which may be hosted on a storage medium and include instructions which can be used to program a general purpose microprocessor or computer to perform processes in accordance with the present invention. This storage medium can include, but is not limited to, any type of disk including floppy disks, optical disks, CD-ROMs, magneto-optical disks, ROMs, RAMs, EPROMs, EEPROMs, flash memory, magnetic or optical cards, or any type of media suitable for storing electronic instructions.

Numerous modifications and variations of the present invention are possible in light of the above teachings. It is therefore to be understood that within the scope of the appended claims, the invention may be practiced otherwise than as specifically described herein.

The invention may also be implemented by the preparation of applications specific integrated units or by interconnecting in an appropriate network of conventional component units, as will be readily apparent to those skilled in the art.

The source of image data to the present invention may be any appropriate image acquisition device such as an x-ray machine, CT apparatus, and an MRI apparatus. Further, the acquired data may be digitized if not already in digital form. Ultimately, the source of image data being obtained in process may be a memory storing data produced by an image acquisition device, and a memory may be local or remote, in which case a data communication network, such as PACS (Picture Achieving Computer System), may be used to access the image data for processing according to the present invention.

Of course, the particular hardware or software implementation of the present invention may be varied while still remaining within the scope of the present invention. It is therefore to be understood that within the scope of the appended claims and their equivalence, the invention may be practice otherwise than as specifically described herein.

Obviously, numerous modifications and variations of the present invention are possible in light of the above teachings. It is therefore to be understood that within the scope of the appended claims, the invention may be practiced otherwise than as specifically described herein.

The invention claimed is:

1. An x-ray computed tomography system that generates an x-ray beam with an x-ray generator and detects with an x-ray detector at least one characteristic of the x-ray beam generated by the x-ray generator, after the x-ray beam has passed through an object, the system comprising:
   a converting unit configured to obtain analog projection data outputted by the x-ray detector and to convert the analog projection data to digital projection data; and
   a processing unit configured to obtain the digital projection data from the converting unit, to detect overflow digital projection data that overflows a measuring range of the computed tomography system, and to correct the overflow digital projection data of the digital projection data by using a curve fitting function.

2. The x-ray computed tomography system of claim 1, wherein the processing unit comprises:
   an overflow unit configured to detect the overflow digital projection data; and
   a correction unit configured to correct the overflow digital projection data based on the overflow digital projection data obtained from the overflow unit, non-overflow digital projection data of the digital projection data obtained from the converting unit, and the curve fitting function of the processing unit.

3. The x-ray computed tomography system of claim 2, wherein the correction unit comprises:
   a first fitting unit configured to perform a first curve fitting function on the non-overflow digital projection data obtained from the converting unit;
   a second fitting unit configured to perform a second function fitting on a combination of the non-overflow digital projection data and the overflow digital projection data obtained from the converting unit and the overflow unit, respectively; and
   a weighting unit configured to weight and combine an output obtained from the first fitting unit and an output obtained from the second fitting unit to output a correction of the digital projection data, wherein a weight is adaptatively calculated by simulation by the weighting unit based on prior known digital projection data of the x-ray computed tomography system or the weight is obtained from a known lookup table.

4. The x-ray computed tomography system of claim 1, further comprising:
a reconstruction unit configured to reconstruct an image of the object based on the corrected digital projection data obtained from the correction unit and the non-overflow digital projection data.

5. The x-ray computed tomography system of claim 4, further comprising:
a display unit configured to display the image of the object reconstructed by the reconstruction unit.

6. The x-ray computed tomography system of claim 3, wherein the correction unit further comprises:
an interpolation unit configured to identify overflow points in the digital projection data obtained from the converting unit and to linearly interpolate a group of overflow points if the group has a number of overflow points smaller than a predetermined number.

7. The x-ray computed tomography system of claim 6, wherein the first and second fitting units correct only groups of overflow points that have a number of overflow points bigger than the predetermined number.

8. The x-ray computed tomography system of claim 7, wherein the predetermined number is one.

9. The x-ray computed tomography system of claim 1, wherein the x-ray detector is an array detector having a plurality of detector elements.

10. The x-ray computed tomography system of claim 6, wherein the overflow unit comprises:
a mapping unit configured to create an overflow map that identifies overflow points in the digital projection data obtained from the converting unit and to provide the overflow map to the correction unit.

11. The x-ray computed tomography system of claim 10, further comprising:
a prior knowledge input unit configured to input the prior known digital projection data of the x-ray computed tomography system to the weighting unit.

12. The x-ray computed tomography system of claim 11, wherein the prior known digital projection data is water calibration data obtained by irradiating water with the x-ray beam in the computed tomography system and measuring with the x-ray detector the at least one characteristic of the x-ray beam after the x-ray beam has passed through the water.

13. The x-ray computed tomography system of claim 12, further comprising:
a prior knowledge correction unit configured to calculate a correction of the overflow digital projection data based on an input obtained from the prior knowledge input data unit and an input obtained from the weighting unit; and
a selection unit configured to select a best correction to be applied to the digital projection data based on an output obtained from the prior knowledge correction unit and an output obtained from the weighting unit.

14. The x-ray computed tomography system of claim 13, wherein
the first curve fitting function is a spline function,
the second curve fitting function is a polynomial function, and
the selection unit selects the smallest correction from the correction of weighting unit, a correction of the second fitting unit, and the correction of the prior knowledge correction unit as the best selection.

15. The x-ray computed tomography system of claim 1, wherein the processing unit comprises a selection unit configured to select a correction algorithm based on characteristics of the overflow.

16. The x-ray computed tomography system of claim 1, wherein the processing unit is configured to correct the digital projection data along a channel direction of the x-ray detector.

17. A method for correcting an image of an object placed in an x-ray computed tomography system that generates an x-ray beam with an x-ray generator and detects with an x-ray detector at least one characteristic of the x-ray beam generated by the x-ray generator, after the x-ray beam has passed through the object, the method comprising:
converting analog projection data outputted by the x-ray detector to digital projection data with a converting unit connected to the x-ray detector;
detecting overflow digital projection data that overflows a measuring range of the computed tomography system with an overflow detecting unit connected to the converting unit; and
correcting the overflow digital projection data with a correction unit connected to the overflow detecting unit by using a curve fitting function to produce a corrected image.

18. The method of claim 17, wherein the correcting comprises:
correcting the overflow digital projection data with the correction unit based on the overflow digital projection data obtained from the overflow detecting unit, non-overflow digital projection data of the digital projection data obtained from the converting unit, and the curve fitting function.

19. The method of claim 18, wherein the correcting further comprises:
performing a first curve fitting function with a first fitting unit on the non-overflow digital projection data obtained from the converting unit;
performing a second curve fitting function with a second fitting unit on a combination of the non-overflow digital projection data obtained from the converting unit and the overflow digital projection data obtained from the overflow detecting unit; and
weighting and combining an output obtained from the first fitting unit and an output obtained from the second fitting unit with a weighting unit to output a correction of the digital projection data,
wherein a weight is adaptatively calculated by simulation by the weighting unit based on prior known digital projection data of the x-ray computed tomography system or the weight is obtained from a known lookup table.

20. The method of claim 17, further comprising:
reconstructing the image of the object with a reconstruction unit, based on the corrected digital projection data and non-overflow digital projection data obtained from the correction unit and the converting unit, respectively.

21. The method of claim 20, further comprising:
displaying the image of the object reconstructed by the reconstruction unit on a display unit.

22. The method of claim 19, wherein the correcting further comprises:
identifying overflow points in the digital projection data obtained from the converting unit with a linear interpolation unit; and linearly interpolating a group of overflow points identified by the linear interpolation unit if the group has a number of overflow points smaller than a predetermined number.

23. The method of claim 22, wherein the first and second fitting units correct only groups of overflow points that have a number of overflow points bigger than the predetermined number.

24. The method of claim 23, wherein the predetermined number is one.

25. The method of claim 17, wherein the x-ray detector is an array detector having a plurality of detector elements.

26. The method of claim 22, further comprising:
creating an overflow map that identifies overflow points in the digital projection data obtained from the converting unit with an overflow map unit; and
providing the overflow map to the correction unit.

27. The method of claim 26, further comprising:
inputting prior known digital projection data of the x-ray computed tomography system into a prior knowledge input unit; and
providing the prior known digital projection data to the weighting unit.

28. The method of claim 27, wherein the prior known digital projection data is water calibration data obtained by irradiating water with the x-ray beam in the computed tomography system and measuring with the x-ray detector the at least one characteristic of the x-ray beam, after the x-ray beam has passed through the water.

29. The method of claim 28, further comprising:
calculating a correction of the overflow digital projection data with a prior knowledge correction unit based on an output obtained from the prior knowledge input data unit and an output obtained from the weighting unit; and
selecting a best correction to be applied to the digital projection data based on an output obtained from the correction unit and an output obtained from the prior knowledge correction unit by using a selection unit that communicates to the correction unit and the prior knowledge correction unit.

30. The method of claim 29, wherein
the first curve fitting function is a spline function,
the second curve fitting function is a polynomial function, and
the selection unit selects the smallest correction from the correction of the weighting unit, a correction of the second fitting unit, and the correction of the prior knowledge correction unit as the best selection.

31. The method of claim 17, wherein the correcting comprises:
selecting a correction method based on characteristics of the overflow with a selection unit connected to the correction unit.

32. The method of claim 17, wherein the correcting comprises:
correcting the digital projection data along a channel direction of the x-ray detector.

33. A computer readable medium for correcting an image of an object placed in an x-ray computed tomography system that generates an x-ray beam with an x-ray generator and detects with an x-ray detector at least one characteristic of the x-ray beam generated by the x-ray generator, after the x-ray beam has passed through the object, the computer readable medium storing instructions for execution on a computer system, which when executed by the computer cause the computer to execute a process comprising:

converting analog projection data outputted by the x-ray detector to digital projection data with a converting unit connected to the x-ray detector;
detecting overflow digital projection data that overflows a measuring range of the computed tomography system with an overflow detecting unit connected to the converting unit; and
correcting the overflow digital projection data with a correction unit connected to the overflow detecting unit by using a curve fitting function to produce the corrected image.

34. The computer readable medium according to claim 33, wherein the correcting comprises:
correcting the overflow digital projection data with the correction unit based on the overflow digital projection data obtained from the overflow detecting unit, non-overflow digital projection data of the digital projection data obtained from the converting unit, and the curve fitting function.

35. The computer readable medium according to claim 34, wherein the correcting further comprises:
performing a first curve fitting function with a first fitting unit on the non-overflow digital projection data obtained from the converting unit;
performing a second curve fitting function with a second fitting unit on a combination of the non-overflow digital projection data obtained from the converting unit and the overflow digital projection data obtained from the overflow detecting unit; and
weighting and combining an output obtained from the first fitting unit and an output obtained from the second fitting unit with a weighting unit to output a correction of the digital projection data,
wherein a weight is adaptatively calculated by simulation by the weighting unit based on prior known digital projection data of the x-ray computed tomography system or the weight is obtained from a known lookup table.

36. The computer readable medium according to claim 33, further comprising:
reconstructing the image of the object with a reconstruction unit, based on the corrected digital projection data and non-overflow digital projection data obtained obtained from the correction unit and the converting unit, respectively.

37. The computer readable medium according to claim 33, further comprising:
displaying the image of the object reconstructed by the reconstruction unit on a display unit.

38. The computer readable medium according to claim 35, wherein the correcting further comprises:
identifying overflow points in the digital projection data obtained from the converting unit with a linear interpolation unit; and
linearly interpolating a group of overflow points identified by the linear interpolation unit if the group has a number of overflow points smaller than a predetermined number.

39. The computer program product according to claim 38, wherein the first and second fitting units correct only groups of overflow points that have a number of overflow points bigger than the predetermined number.

40. The method of claim 39, wherein the predetermined number is one.

41. The computer readable medium according to claim 33, wherein the x-ray detector is an array detector having a plurality of detector elements.

42. The computer readable medium according to claim 38, further comprising:
   creating an overflow map that identifies overflow points in the digital projection data with an overflow map unit; and
   providing the overflow map to the correction unit.

43. The computer readable medium according to claim 42, further comprising:
   inputting prior known digital projection data of the x-ray computed tomography system into a prior knowledge input unit; and
   providing the prior known digital projection data to the weighting unit.

44. The computer readable medium according to claim 43, wherein the prior known digital projection data is water calibration data obtained by irradiating water with the x-ray beam in the computed tomography system and measuring with the x-ray detector the at least one characteristic of the x-ray beam, after the x-ray beam has passed through the water.

45. The computer readable medium according to claim 44, further comprising:
   calculating a correction of the overflow digital projection data with a prior knowledge correction unit based on an output obtained from the prior knowledge input data unit and an output obtained from the weighting unit; and
   selecting a best correction to be applied to the digital projection data based on an output obtained from the correction unit and an output obtained from the prior knowledge correction unit by using a selection unit that communicates to the correction unit and the prior knowledge correction unit.

46. The computer readable medium according to claim 45, wherein
   the first curve fitting function is a spline function,
   the second curve fitting function is a polynomial function, and
   the selection unit selects the smallest correction from the correction of the weighting unit, a correction of the second fitting unit, and the correction of the prior knowledge correction unit as the best selection.

47. The computer readable medium according to claim 33, wherein the correcting comprises:
   selecting a correction method based on characteristics of the overflow with a selection unit connected to the correction unit.

48. The computer readable medium according to claim 33, wherein the correcting comprises:
   correcting the digital projection data along a channel direction of the x-ray detector.

* * * * *